United States Patent
Paape

(10) Patent No.: US 7,045,510 B2
(45) Date of Patent: May 16, 2006

(54) METHODS FOR PREVENTION AND TREATMENT OF MASTITIS

(75) Inventor: Max J. Paape, Silver Spring, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 10/895,797

(22) Filed: Jul. 21, 2004

(65) Prior Publication Data

US 2006/0019926 A1   Jan. 26, 2006

(51) Int. Cl.
*A61K 31/721* (2006.01)
(52) U.S. Cl. ...................................................... 514/59
(58) Field of Classification Search ................... 514/59
See application file for complete search history.

(56) References Cited

OTHER PUBLICATIONS

Krdzalic et al, Veterinarski Glasnik, 1983, 37(12), 949-954.*
Zdravlje Leskovac, 2001, pp. 1-2; www.zdravlje.co.yu/vetadex.htm.*
McDonald, J.S. et al, J. Am. Vet. Res. 1981, 42(8), 1360-1365.*
Bannerman et al Feed Information News, Jan. 27, 2004, pp. 1-6.*
McDonald, J.S., et al., "Total and Differential Somatic Cell Counts in Secretions from Noninfected Bovine Mammary Glands: The Early Nonlactating Period", *Am. J. Vet. Research.*, vol. 42(8), pp. 1360-1365, Aug., 1981.
Paape, M.J., et al., "Update on the Use of Intramammary Devices in the Control of Mastitis", 25$^{th}$ *Annual Meeting National Mastitis Council, Inc.*, Columbus, OH, Feb. 9-12, 1986.
Max Paape, "Recent Advances in the Control of Mastitis in dairy Cows", *TEDCO Federal Lab Program: Bioscience for Today and Beyond: Innovative Technologies for a Growing World Technology Showcase*, Henry A. Wallace Beltsville Agricultural Research Center, pp. 1-8, Apr. 15, 2003.
Bannerman, D.D., et al., "Recent Advances in the Control of Mastitis in Dairy Cows", *Feed Information News Service*, 6 pages, Jan. 27, 2004.

* cited by examiner

*Primary Examiner*—Shaojia A. Jiang
*Assistant Examiner*—Ganapathy Krishnan
(74) *Attorney, Agent, or Firm*—John Fado; G. Byron Stover

(57) ABSTRACT

A method of preventing or treating mastitis in a mammal, involving administering to the mammal a therapeutically effective amount of diethylaminoethyl-dextran (DEAE-dextran) or dextran.

13 Claims, 1 Drawing Sheet

METHODS FOR PREVENTION AND TREATMENT OF MASTITIS

BACKGROUND OF THE INVENTION

The present invention relates to methods of preventing or treating mastitis in a mammal, involving administering to the mammal a therapeutically effective amount of diethylaminoethyl-dextran (DEAE-dextran) or dextran.

The treatment and prevention of mastitis in dairy cows continues to be of primary importance to those engaged in the dairy farming industry. The combined costs of mastitis to the U.S. dairy farming industry have been estimated at over two billion dollars annually.

Mastitis is caused by infections of the mammary, or milk-producing, glands by a broad spectrum of pathogenic microorganisms. In particular, when the milk-producing glands and surrounding tissues in the udder become infected, the tissues become inflamed with cellular infiltrates and associated toxic substances. The cellular infiltrates and associated toxins, along with the infecting organisms themselves, can cause a dramatic reduction in the quality of milk produced by the animal. The infiltrates, toxins, and microorganisms can also affect the quantity of milk produced by the animal, possibly even resulting in the stoppage of production. Occasionally, the infection can spread systemically to other organ and tissue sites via the blood or lymphatic systems. The spreading infection can, in extreme cases, seriously debilitate or kill the infected animal.

Given the importance of the mastitis problem to dairy farmers, several methods have been proposed to combat this problem. One method frequently used to combat the problem has been to "cull" out or separate the infected animals from the herd, and then to treat the infected animals with antibiotics. Antibiotics can be administered either directly (via an injection) or indirectly (via feed). However, the secondary problem of antibiotic residues in the treated animals and their milk products has come under increased scrutiny from federal and state regulatory agencies. Additionally, public outcry over the use of antibiotics and the presence of antibiotics residues in meat and milk products has severely limited the market for such products.

Thus there is a need to find an alternative to, and decrease the dependence on, antibiotics in managing udder health of lactating mammals such as dairy cows.

SUMMARY OF THE INVENTION

In accordance with the present invention there is provided a method of preventing or treating mastitis in a mammal, involving administering to the mammal a therapeutically effective amount of diethylaminoethyl-dextran (DEAE-dextran) or dextran.

DETAILED DESCRIPTION OF THE INVENTION

Figure 1:
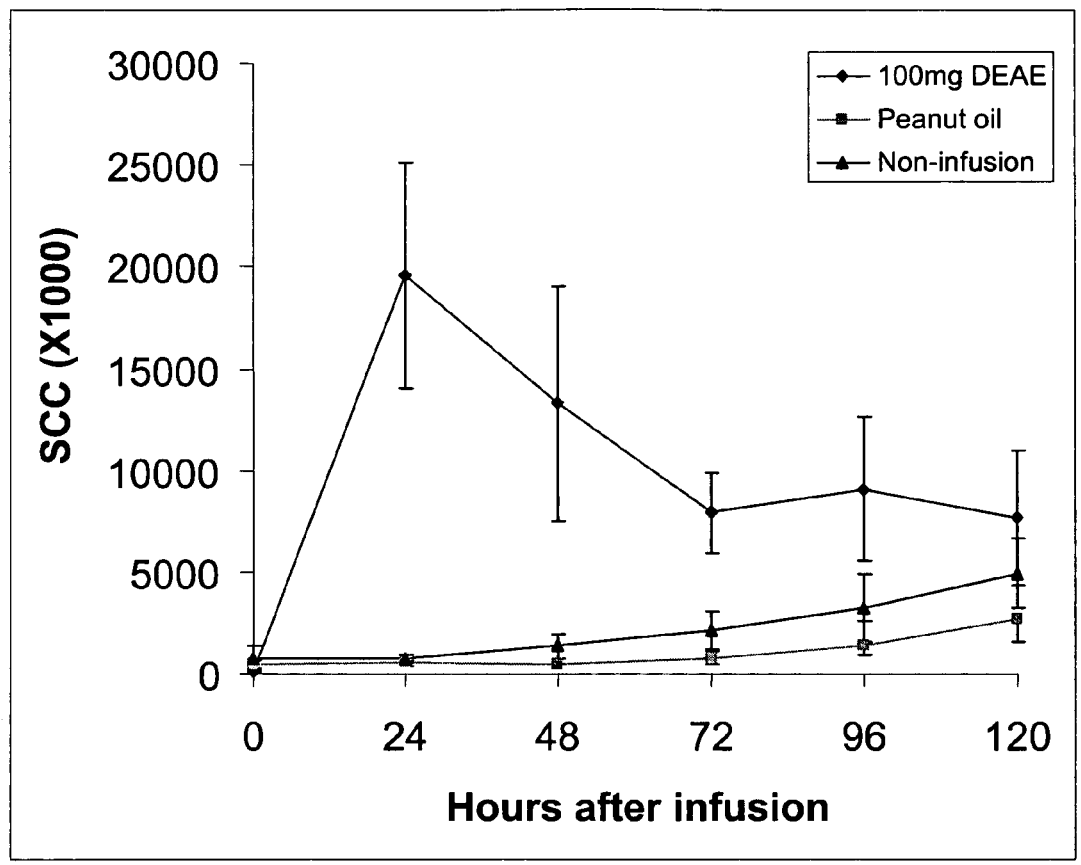
FIG. 1 shows milk somatic cell concentration (SCC) after infusion to dairy cows of DEAE-dextran, peanut oil, or non-infusion.

The present invention relates to a method of preventing or treating mastitis in a mammal (e.g., cow, goat, ewe), involving administering to the mammal a therapeutically effective amount of diethylaminoethyl-dextran (DEAE-dextran) or dextran.

In a dairy herd, 50% of the intramammary infections develop during the nonlactating period of the lactation cycle known as the dry period. The standard management practice to reduce the number of infections during the nonlactating period is to administer a long lasting and concentrated antibiotic preparation immediately after the last milking preceding the dry period. While this procedure has been effective, it is undesirable from a food safety standpoint. Due to human error, milk tainted with this formulation occasionally becomes commingled with milk intended for the market, and subsequently it must be discarded. This results in a significant economic loss to the dairy producer. In addition, the widespread use of antibiotics is undesirable from the standpoint of creating a population of cattle which may be resistant to antibiotics typically used to treat cattle disease.

Dairy cows are milked for about 305 days and go into a period of non-lactation (dry period) for about 60 days. During the first several days of the dry-period, the mammary gland is very susceptible to infection because the white blood cell count in milk is very low (McDonald and Anderson, Am. J. Vet. Res., 42:1366–1368 (1980)). If the gland should become infected there is nothing to keep the bacteria from growing and ultimately resulting in an intramammary infection. It takes about 4–6 days from dry off for the white blood cells in milk to reach levels that are protective; we have previously shown that about 900,000 white blood cells/ml of milk is 90% effective in preventing mastitis (Paape et al., Update on the use of intramammary devices in the control of mastitis, Proceedings of the 25th Annual Meeting of the National Mastitis Council, Inc., 1986, pp 87–103).

The active agent of the present invention is generally dextran or diethylaminoethyl-dextran (DEAE-Dextran) which is a polycationic derivative of dextran. Generally, a therapeutically effective amount of the active agent is administered to the mammal. A "therapeutically effective amount" of active agent is a dose sufficient to either prevent or treat mastitis in a mammal to which the active agent is administered. The dosages of the active agent which can treat or prevent mastitis can be determined in view of this disclosure by one of ordinary skill in the art by running routine trials with appropriate controls. Comparison of the appropriate treatment groups to the controls will indicate whether a particular dosage is effective in preventing or treating a disease (e.g., mastitis) used in a controlled challenge. It is understood in the art that the amount of active agent administered should be the amount that is effective to control the particular pathogen or pathogens in question. In addition, the type, size and condition of the host being treated must be taken into consideration. For example, when controlling a pathogen responsible for mastitis, the dose will vary depending on the type and size of the mammal (e.g., ruminant) being treated. An effective amount may be achieved by a single dose or multiple dosings.

When administered intramammarily, the active agent is administered by injection into the mammary gland, typically by infusion into the teat through the milk canal. The dosage of the active agent by intramammary injection is from about 50 mg to about 400 mg, preferably from about 100 mg to about 200 mg.

Beyond dosage, an effective administration of the active agent according to the present invention will in part depend on the number and timing of the dosages. For example, the active agent is typically given once, though multiple administrations of a dosage may be given to an animal, typically at least about 24 hours apart. In some circumstances it may be desirable to administer the active agent more than once to the animal. Again, it is believed that the precise combination of dosage and timing will be subject to a wide range of variation and that numerous combinations effective in treating or preventing a disease can be readily established by those of ordinary skill in the art in view of the present disclosure.

The active agent (e.g., DEAE-dextran) of the subject invention can be given to a mammal either after the onset of mastitis, thus serving as a treatment, or prior to the onset of mastitis, thus serving as a preventive measure. The preventive use of the subject invention is particularly important, for instance, in case mastitis has been detected in some animals in the same herd. It is often desirable to treat all animals in same herd affected in order to eliminate the infection from the whole herd.

The active agent (e.g., DEAE-dextran) is first dissolved in sterile filtered distilled water (e.g., 100 mg per 1 ml of water), then one ml is suspended in 9 ml of a carrier (e.g., peanut oil). Peanut oil, which is also used in antibiotics given at dry-off, allows for a slow release of the active agent over a period of several weeks. At calving, milk is discarded for six milkings so the peanut oil is not in milk that goes into the bulk tank for human consumption; thus, there is no danger to people who may be allergic to peanuts. Known carriers (e.g., pharmaceutically acceptable carriers) other than peanut oil could also be utilized, such as mineral oil, vegetable oil, 3% cabosil in peanut oil, 2% aluminum monostearate in peanut oil, 25% polyethylene glycol in either mineral oil, vegetable oil or peanut oil.

DEAE-dextran is a mild irritant and when injected into the mammary gland it will increase the white blood cell count in the milk to levels that will protect against infection.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Experimental Design: At dry-off all quarters of even numbered cows (n=39) were infused with antibiotics (Cefa-Dri (Fort Dodge Animal Health, Fort Dodge, Iowa 50501) containing 300 mg cephapirin benzathineidentify activity in peanut oil) approved for use by FDA. All quarters of odd numbered cows (n=40) were infused with dextran (total dose 100 mg DEAE-dextran (Sigma Chemical Co. St. Louis, Mo.)) in 1 ml of sterile filtered distilled water and suspended in 9 ml of peanut oil (Sigma). This level of dextran increased milk somatic cell concentration (SCC) to one million cells per ml with no clinical symptoms (e.g., swelling, elevated body temperature, redness of udder, pain)(FIG. 1).

Mammary quarters of 4 dairy cows at drying-off were infused with either 100 mg of DEAE-dextran, peanut oil, or were uninfused. Secretions were collected at 0, 24, 48, 72, 96, and 120 hours post infusion for determination of milk somatic cell concentration. Somatic cell counts for dextran infused quarters increased from $129 \times 10^3$/ml at 0 hour to $19,591 \times 10^3$/ml at 24 hours, and decreased to $8,000 \times 10^3$/ml at 72 hours, and remained at 8,000 to $9,000 \times 10^3$/m until 120 hours. Non-infused quarters averaged $775 \times 10^3$ cells/ml at 0 hour and gradually increased to $5,000 \times 10^3$ cells/ml at 120 hours. Quarters infused with peanut oil averaged $457 \times 10^3$ cells/ml at 0 hour and gradually increased to $1,100 \times 10^3$ cells/ml at 120 hours.

Intramammary infection status before dry-off and after calving for 39 cows that were infused with antibiotics in all 4 mammary quarters at the time of dry-off are shown in Table 1. There were 16 infected quarters at dry-off. After calving 4 of the 16 quarters remained infected (old infections) and 28 quarters became infected during the dry period (new infections) for a total of 32 infections. When compared to the number of infected quarters (16 quarters) at the time of dry-off, this represented a net gain of 16 intramammary infections. For the subsequent lactation milk yield averaged 25,424 pounds.

Intramammary infection status before dry-off and after calving for 40 cows that were infused with dextran in all 4 mammary quarters at the time of dry-off are shown in Table 2. There were 38 infected quarters at dry-off. After calving 17 of the 38 quarters remained infected (old infections) and 26 quarters became infected during the dry period (new infections) for a total of 43 infections. When compared to the number of infected quarters at the time of dry-off (38 quarters), this resulted in a net gain of 5 intramammary infections. For the subsequent lactation milk yield per cow averaged 26,029 pounds, approximately 700 pounds more than cows that received antibiotics.

All of the references cited herein are incorporated by reference in their entirety. Also incorporated by reference in their entirety are the following references: Paape, M. J., Recent advances in the control of mastitis in dairy cows, Proceedings of Bioscience for Today and Beyond: Innovative Technologies for a Growing World, Beltsville Agriculture Research Center, USDA, Beltsville, Md., Apr. 14, 2003; Bannerman, D., and Paape, M. J., Recent advances in the control of mastitis in dairy cows, Feed Information News Service, Jan. 27, 2004; U.S. patent application Ser. No. 10/184,005 filed on 27 Jun. 2002

Thus, in view of the above, the present invention concerns (in part) the following:

A method of preventing or treating mastitis in a mammal, comprising (or consisting essentially of or consisting of) administering to the mammal a therapeutically effective amount of diethylaminoethyl-dextran (DEAE-dextran) or dextran.

The above method, wherein the administering is done prior to the onset of the infection.

The above method, wherein the administering is done after the onset of the infection.

The above method, wherein the mammal is a cow, goat, or ewe.

The above method, wherein the mammal is a cow.

The above method, wherein the administering is via intramammary injection.

The above method, wherein the diethylaminoethyl-dextran or dextran is administered in an amount from about 50 mg to about 400 mg.

The above method, wherein the diethylaminoethyl-dextran or dextran is administered in an amount from about 100 mg to about 200 mg.

The above method, said method comprising (or consisting essentially of or consisting of) administering to the mammal a therapeutically effective amount of diethylaminoethyl-dextran.

The above method, wherein the administering is during the dry period of said mammal Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Antibiotics

| | | Infection status (quarters) | | yearly milk yield |
|---|---|---|---|---|
| | | after dry-off | | |
| Cow # | before dry-off | old infection | new infection | (pounds) |
| 194 | clean | clean | clean | N/A |
| 1230 | clean | clean | clean | N/A |
| 1412 | clean | clean | RF, RR, LF, LR CNS | 21560 |
| 1504 | clean | clean | clean | 27970 |
| 1614 | clean | clean | LF CNS | 28170 |
| 1630 | clean | clean | RF CNS | 24330 |
| 1642 | clean | clean | clean | 23670 |
| 1644 | clean | clean | LR CNS | 23590 |
| 1650 | clean | clean | LF *Strep.* spp. | 23540 |
| 1652 | RF CNS | clean | clean | 21290 |
| 1678 | clean | clean | clean | 28100 |
| 1688 | clean | clean | clean | 26210 |
| 1692 | LF Gram - | clean | clean | 21880 |
| 1698 | LR CNS | clean | RF, LF CNS | 26730 |
| 1714 | clean | clean | RF, RR, LR CNS | 31560 |
| 1800 | clean | clean | clean | 24650 |
| 1802 | RR CNS | clean | clean | 29290 |
| 1806 | clean | clean | clean | 31880 |
| 1816 | clean | clean | LR Yeast | 14900 |
| 1850 | LR CNS | LR CNS | LR, RR CNS, LF *C. pyrogenes* | 28780 |
| 1860 | LR Gram - | clean | clean | 27840 |
| 1874 | RR CNS, LR Yeast | RR CNS | LF Gram - | 25580 |
| 1876 | LF *S. aureus*, RR CNS | clean | RF CNS | 24370 |
| 1884 | RR, LR CNS | LR CNS | clean | 31920 |
| 1898 | clean | clean | clean | 25100 |
| 2014 | clean | clean | clean | 10350 |
| 2024 | clean | clean | RR CNS | 28430 |
| 2028 | clean | clean | LR *C. bovis* | 23900 |
| 2030 | clean | clean | clean | 23750 |
| 2040 | clean | clean | LR CNS | 28590 |
| 2044 | clean | clean | RF CNS | 25000 |
| 2046 | clean | clean | RR CNS | 27810 |
| 2050 | RR CNS | clean | LF *C. bovis* | 28490 |
| 2052 | clean | clean | RF *S. aureus* | 21230 |
| 2068 | clean | clean | RF, LF *Strep.* Spp. | 27830 |
| 2070 | LR CNS | clean | clean | 24510 |
| 2074 | LR CNS | clean | clean | 27780 |
| 2094 | clean | clean | clean | 29800 |
| 2096 | RR CNS | RR CNS | LR CNS | 20300 |
| | | | | Mean 25424 |
| 39 cows | 16 quarters infected | 4 old infections | 28 new infections | |
| | | 32 total infections (net gain of 16) | | |

N/A = not available
Clean = no bacteria
CNS = coagulase negative *Staphylococci*
*S. aureus* = *Staphylococcus aureus*
*C. bovis* = *Corynebacterium bovis*
Gram - = Gram negative bacteria
*C. pyrogenes* = *Corynebacterium pyrogenes*
*Strep.* spp. = *Streptococci* species

TABLE 2

Dextran

| | | Infection status (quarters) | | yearly milk yield |
|---|---|---|---|---|
| | | after dry-off | | |
| Cow # | before dry-off | old infection | new infection | (pounds) |
| 193 | RR CNS | RR CNS | RF Yeast | N/A |
| 537 | clean | clean | LR *C. bovis* | 23770 |
| 1291 | LF CNS | clean | RR CNS | 28540 |
| 1435 | clean | clean | RF CNS | 24990 |
| 1489 | clean | clean | clean | 19640 |
| 1621 | clean | clean | LR Gram -, RR, CNS | 27420 |
| 1627 | LF CNS | clean | clean | 22960 |
| 1629 | RR, LF CNS | LF CNS | LR CNS | N/A |
| 1685 | clean | clean | RR, LR CNS | 27540 |
| 1691 | RF, RR, CNS | RF, RR CNS | LF, LR CNS | 24330 |
| 1695 | LF CNS | clean | LR *C. pyrogenes* | 24530 |
| 1699 | RR, LF, LR CNS | clean | clean | 28040 |
| 1819 | LF *S. aureus* | LF *S. aureus* | RF, LR, LF *S. aureus* | 20340 |
| 1827 | RF, RR, LF, LR CNS | RF, RR, LF, LR CNS | | 27920 |
| 1828 | clean | clean | LF *C. pyrogenes* | 22850 |
| 1843 | clean | clean | LF CNS | 25820 |
| 1855 | clean | clean | clean | 27620 |
| 1859 | RR *S. aureus*, LR CNS | RR *S. aureus* | RF *S. aureus* | 15960 |
| 1867 | clean | clean | clean | 19190 |
| 1883 | RF, RR CNS | RR CNS | RF *S. aureus* | N/A |
| 1889 | RR, LF *S. aureus* RF,LR CNS | RR, LF *S. aureus* | clean | 27010 |
| 1894 | LR CNS | LR CNS | clean | 22270 |
| 1899 | RF, LF CNS | clean | RR, LR *S. aureus* | 29870 |
| 2005 | LF, LR CNS | clean | clean | 29550 |
| 2007 | clean | clean | LR Gram - | 25740 |
| 2025 | clean | clean | RF, LF CNS | 37000 |
| 2033 | clean | clean | clean | 34230 |
| 2035 | RF CNS | RF CNS | clean | 27260 |
| 2045 | RF, RR, LF, LR CNS | RF, LR CNS | clean | 20510 |
| 2059 | clean | clean | clean | 26660 |
| 2061 | LR CNS | clean | clean | 30380 |
| 2063 | clean | clean | clean | 31500 |
| 2065 | RR CNS | clean | clean | 27680 |
| 2071 | clean | clean | clean | 17630 |
| 2083 | clean | clean | clean | 29230 |
| 2089 | clean | clean | clean | 25200 |
| 2095 | clean | clean | clean | 31200 |
| 2207 | LR *C. bovis* | clean | LR CNS | 27950 |
| 3353 | clean | clean | RR CNS | 24950 |
| 9811 | RR CNS | clean | clean | 25780 |
| | | | | Mean 26029 |
| 40 cows | 38 quarters infected | 17 old infections | 26 new infections | |
| | | 43 total infections (net gain of 5) | | |

N/A = not available
Clean = no bacteria
CNS = coagulase negative *Staphylococci*
*S. aureus* = *Staphylococcus aureus*
*C. bovis* = *Corynebacterium bovis*
Gram - = Gram negative bacteria
*C. pyrogenes* = *Corynebacterium pyrogenes*
Strep. spp. = *Streptococci* species

I claim:

1. A method of treating or reducing the incidence of mastitis in a mammal, comprising administering to said mammal a therapeutically effective amount of diethylaminoethyl-dextran or dextran, wherein said method does not involve the use of antibiotics.

2. The method of claim 1, wherein said administering is done prior to the onset of the infection.

3. The method of claim 1, wherein said administering is done after the onset of the infection.

4. The method of claim 1, wherein said mammal is a cow, goat, or ewe.

5. The method of claim 4, wherein said mammal is a cow.

6. The method of claim 1, wherein said administering is via intramammary injection.

7. The method of claim 1, wherein said diethylaminoethyl-dextran or dextran is administered in an amount from about 50 mg to about 400 mg.

8. The method of claim 1, wherein said diethylaminoethyl-dextran or dextran is administered in an amount from about 100 mg to about 200 mg.

9. The method of claim 1, said method comprising administering to said mammal a therapeutically effective amount of diethylaminoethyl-dextran.

10. The method of claim 1, wherein said administering is during the dry period of said mammal.

11. The method of claim 1, wherein said method consists essentially of administering to said mammal a therapeutically effective amount of diethylaminoethyl-dextran or dextran.

12. The method of claim 1, wherein said method consists of administering to said mammal a therapeutically effective amount of diethylaminoethyl-dextran or dextran.

13. A method of treating or reducing the incidence of mastitis in a mammal, consisting essentially of administering to said mammal a therapeutically effective amount of diethylaminoethyl-dextran or dextran.

* * * * *